US00PP19783P2

(12) United States Plant Patent
Danziger

(10) Patent No.: US PP19,783 P2
(45) Date of Patent: Mar. 3, 2009

(54) *JAMESBRITTENIA* PLANT NAMED 'DANBRIT8'

(50) Latin Name: *Jamesbrittenia hybrida*
Varietal Denomination: DANBRIT8

(76) Inventor: Gabriel Danziger, PO Box 24, Moshav Mishmar Hashiva, Beit Dagan (IL), 50297

( * ) Notice: Subject to any disclaimer, the term of this patent is extended or adjusted under 35 U.S.C. 154(b) by 0 days.

(21) Appl. No.: 12/008,422

(22) Filed: Jan. 11, 2008

(51) Int. Cl.
*A01H 5/00* (2006.01)

(52) U.S. Cl. ..... Plt./485

(58) Field of Classification Search ..... Plt./485, Plt./263
See application file for complete search history.

*Primary Examiner*—Annette H Para
*Assistant Examiner*—S. B. McCormick-Ewoldt

(57) ABSTRACT

A new and distinct *Jamesbrittenia* cultivar named 'Danbrit8' is disclosed, characterized by having large, red flowers, with a distinct darker halo in the center, a compact, mounded and upright plant habit and continuous flowering. The new variety is a *Jamesbrittenia,* normally produced as an outdoor garden or container plant.

2 Drawing Sheets

Latin name of the genus and species: *Jamesbrittenia hybrida.*
Variety denomination: 'Danbrit8'.

BACKGROUND OF THE INVENTION

The new cultivar is a product of a planned breeding program conducted by the inventor, Gabriel Danziger, in Moshav Mishmar Hashiva, Israel. The objective of the breeding program was to produce plants of *Jamesbrittenia hybrida* with compact habits and large red flowers. The seed parent is the unpatented, proprietary seedling variety referred to as *Jamesbrittenia hybrida* 'cv.5-590. The pollen parent is the unpatented, proprietary seedling variety referred to as *Jamesbrittenia hybrida* 'cv.6-675. The new variety was discovered in August 2006 by the inventor in a group of seedlings resulting from that crossing, in Moshav Mishmar Hashiva, Israel.

Asexual reproduction of the new cultivar 'Danbrit8' by vegetative cuttings was first performed at a commercial greenhouse in Moshav Mishmar Hashiva, Israel in September 2006 and has shown that the unique features of this cultivar are stable and reproduced true to type on successive generations.

SUMMARY OF THE INVENTION

The cultivar 'Danbrit8' has not been observed under all possible environmental conditions. The phenotype may vary somewhat with variations in environment such as temperature, day length, and light intensity, without, however, any variance in genotype.

The following traits have been repeatedly observed and are determined to be the unique characteristics of 'Danbrit8.' These characteristics in combination distinguish 'Danbrit8' as a new and distinct *Jamesbrittenia* cultivar:

1. Compact plant habit.
2. Very large flowers.
3. Unique flower color of red with a large yellow center surrounded by a darker halo.

Plants of the new cultivar 'Danbrit8' are similar to plants of the seed parent, *Jamesbrittenia hybrida* 'cv.5-590' in most horticultural characteristics, however, plants of the new cultivar 'Danbrit8' produce darker flowers with a larger yellow center. Additionally, plants of 'Danbrit8' are more branched, grow more vigorously and are more mounded in habit than the female parent.

Plants of the new cultivar 'Danbrit8' are similar to plants of the commercial variety 'Danbrit1, U.S. Plant Pat. No. 18,193 in most horticultural characteristics, however, plants of the new cultivar 'Danbrit8' have larger flowers, of a darker red. The new variety also has a more upright plant habit and larger leaves than 'Danbrit1.'

BRIEF DESCRIPTION OF THE PHOTOGRAPH

Figure 1:
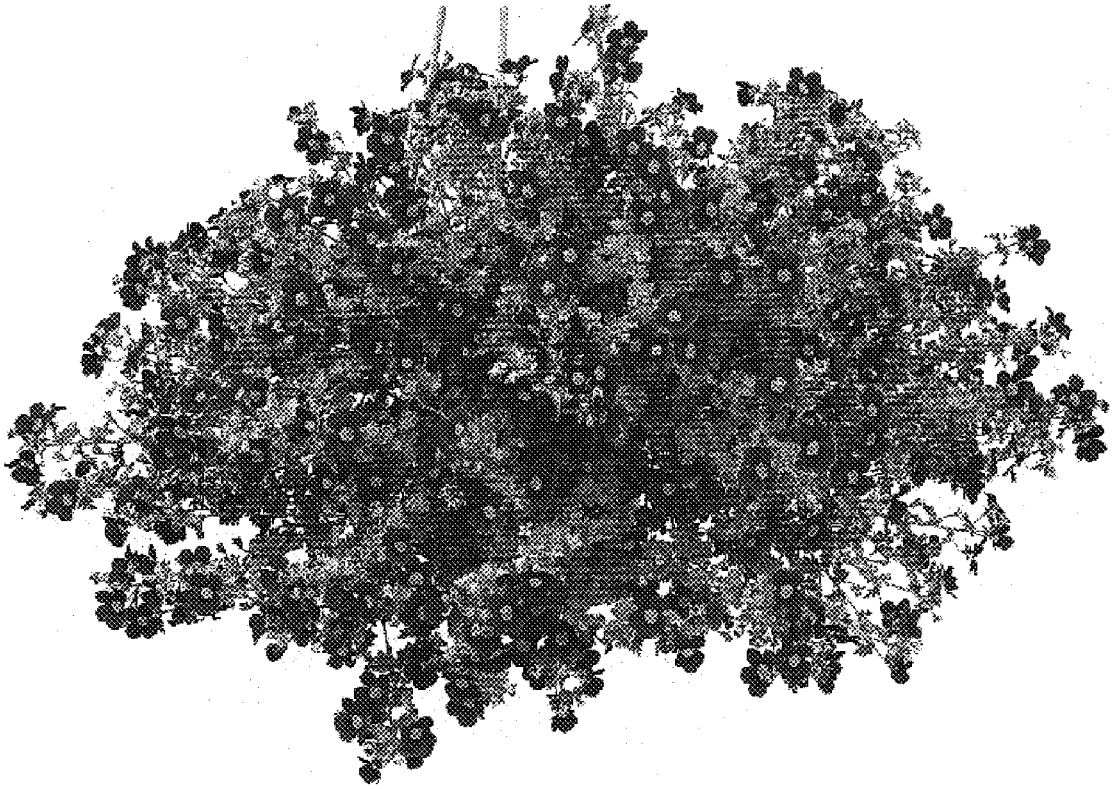

The accompanying photograph in FIG. 1 illustrates in full color a typical plant of 'Danbrit8' grown in a greenhouse, in a 13 cm basket. Age of the plant photographed is approximately 3 months s from a rooted cutting.

Figure 2:
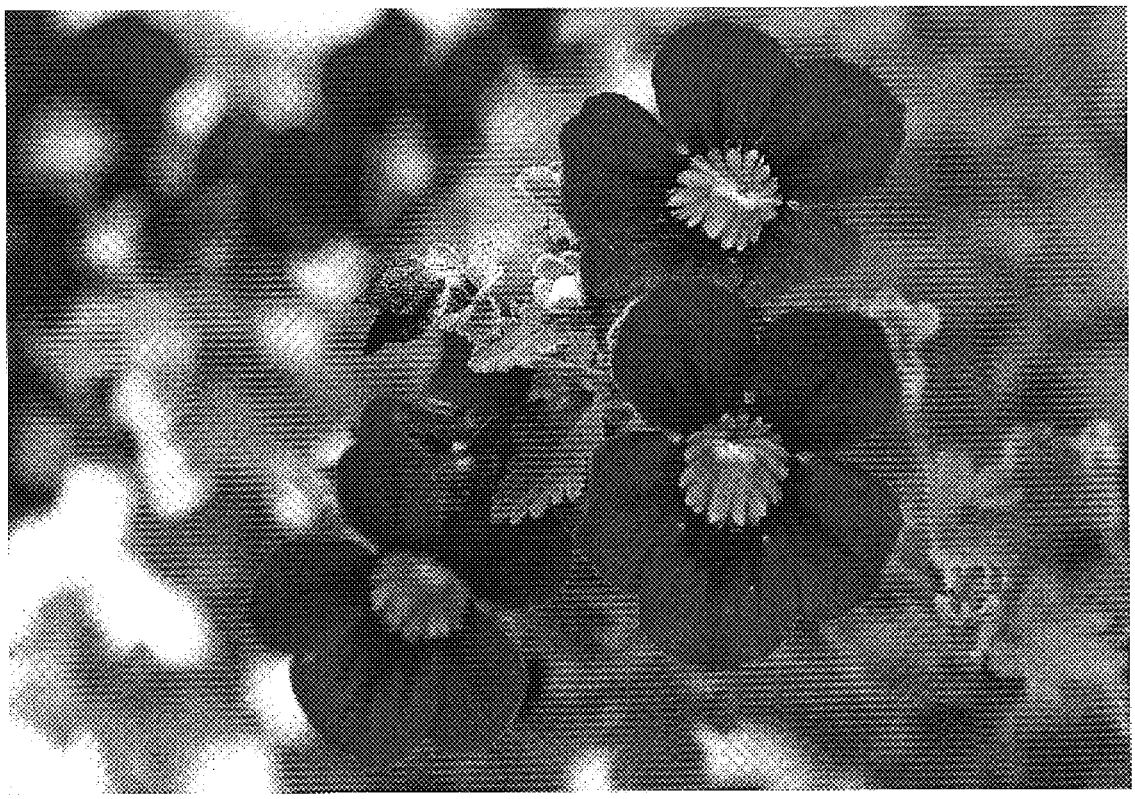

FIG. 2 illustrates in full color a close up of a typical bloom of 'Danbrit8.'

The photographs were taken using conventional techniques and although colors may appear different from actual colors due to light reflectance it is as accurate as possible by conventional photographic techniques.

DETAILED BOTANICAL DESCRIPTION

In the following description, color references are made to The Royal Horticultural Society Colour Chart except where general terms of ordinary dictionary significance are used. The following observations and measurements describe 'Danbrit8' plants grown in a greenhouse in Moshav Mishmar Hashiva, Israel. The growing temperature ranged from 18° C. to 24° C. The greenhouse is subject to partial shade. General light conditions are bright, normal sunlight, with some shade during the brightest part of the day. Measurements and numerical values represent averages of typical plant types.

Botanical classification: *Jamesbrittenia hybrida* cultivar 'Danbrit8.'

PROPAGATION

Time to initiate roots: About 7 to 10 days at approximately 18° C.
Root description: Fine, densely fibrous.
Time to produce a rooted cutting: About 14 to 18 days at 18° C.

PLANT

Growth habit: Mounding annual.
Pot size of plant described: 13 cm.
Age of plant described: Approximately 90 days from a rooted cutting.
Height:
*To top of foliage.*—Approximately 20 cm.
Plant spread: Approximately 55 cm.
Growth rate: Moderate.
Branching characteristics: Well-branched, all branches occurring at ground level, there is no central or main branch.
Length of primary lateral branches: Approximately 20 cm.
Diameter of lateral branches: Approximately 0.2 cm.
Quantity of primary lateral branches: About 10.
Characteristics of primary lateral branches:
*Form.*—Cylindrical.
*Color.*—Near RHS Yellow-Green 146C.
*Texture.*—Slightly pubescent.
*Strength.*—Strong.
Internode length: Approximately 2 cm.

FOLIAGE

Leaf:
*Arrangement.*—Opposite.
*Quantity.*—Approximately 50 per branch.
*Average length.*—Approximately 2.5 cm.
*Average width.*—Approximately 1.5 cm.
*Shape of blade.*—Ovate.
*Apex.*—Obtuse.
*Base.*—Acuminate.
*Margin.*—Serrate.
*Texture of top surface.*—Velvety.
*Pubescence.*—Slightly pubescent.
*Foliage fragrance.*—Lemony.
*Color.*—Young foliage upper side: Near RHS Green 137B. Young foliage under side: Near RHS Green 137C. Mature foliage upper side: Near RHS Green 137A. Mature foliage under side: Near RHS Green 137B.
*Venation.*—Type: Pinnate. Venation color upper side: Near RHS Green 137A. Venation color under side: Near RHS Green 137C.
*Petiole.*—Length: Approximately 0.7 cm. Diameter: Approximately 0.1 cm. Color: Near RHS Green 137C. Texture: Velvety.

FLOWER

Natural flowering season: Freely flowering under outdoors growing conditions with substantially continuous blooming from spring through autumn. Year round in greenhouse environment, or under warm conditions and high sunlight. Flowering begins approximately 6 weeks after planting a rooted cutting.
Inflorescence and flower type and habit: Individual flowers are typical scrophulariaceae shape, 2-lipped, 5-petaled solitary flowers, fused at base, occurring in the leaf axis, on a terminal raceme.
Rate of flower opening: Approximately 4 days from bud to fully opened flower.
Flower longevity on plant: Individual flowers last 7 days on the plant.
Flower form: Salvaform.
Flower size:
*Diameter.*—Approximately 2 cm.
*Length.*—Approximately 1 cm.
*Corolla tube diameter.*—Approximately 0.2 cm.
Corolla/petals:
*Arrangement.*—5 rounded and gameopetalous petals.
*Length.*—About 0.8 cm.
*Width.*—About 0.7 cm.
*Quantity.*—5.
*Texture.*—Velvety.
*Apex.*—Obtuse.
*Base.*—Fused.
*Margin.*—Entire.
Color: When opening:
*Upper surface.*—Near RHS Red 53A.
*Lower surface.*—Near RHS Red 53B.
*Fully opened.*—
*Upper surface.*—Near RHS Red 46A; halo just darker than 46A, same shade. Yellow center RHS 25A.
*Lower surface.*—Near RHS Red 53B.
Corolla tube color: Near RHS yellow-Green 145B.
Bud:
*Shape.*—Slightly flattened sphere.
*Length.*—Approximately 0.7 cm.
*Diameter.*—Approximately 0.4 cm.
*Color.*—Near RHS Red 53A.
Calyx/sepals:
*Quantity per flower.*—5, fused at base.
*Shape.*—Oblong.
*Length.*—Approximately 0.4 cm.
*Width.*—Approximately 0.1 cm.
*Apex.*—Mucronulate.
*Base.*—Fused.
*Margin.*—Entire.
*Texture.*—Velvety.
*Color.*—Upper Surface: Near RHS Green 137C. Lower Surface: Near RHS Green 137C.
Peduncle: None.
Pedicel:
*Length.*—Approximately 1 cm.
*Diameter.*—Approximately 0.1 cm.
*Color.*—Near RHS Green 143C.
*Orientation.*—Slanted upward at an angle of about 45°.
Fragrance: Lemony.

REPRODUCTIVE ORGANS

Stamens:
*Number.*—4.
*Filament length.*—Approximately 0.5 cm.
*Filament color.*—Near RHS Yellow-Green N144A.
Anthers:
*Shape.*—Cylindrical.
*Length.*—Approximately 0.1 cm.
*Color.*—Near RHS Yellow-Orange 15B.
*Pollen.*—Color: Near RHS Yellow-Orange 15B. Quantity: Scarce.

Pistil:

*Number.*—1.

*Length.*—Approximately 0.6 cm.

*Width.*—Approximately 0.1 cm.

*Style.*—Length: Approximately 0.4 cm. Color: Near RHS Green-Yellow 1C.

*Stigma.*—Shape: Round. Color: Near RHS Green 141B.

*Ovary.*—Position: Superior. Shape: Ellipsoid. Color: Near RHS Yellow-Green 150C. Size: About 0.2 cm.

OTHER CHARACTERISTICS

Seeds and fruits: Dark brown, rounded, approximately 0.05 cmin diameter.

Disease/pest resistance: Good resistance to pathogens and pests common to *Jamesbrittenia.*

Temperature tolerance: The new variety tolerates temperatures between 5 to 35° C.

What is claimed is:

1. A new and distinct cultivar of *Jamesbrittenia* plant named 'Danbrit8' as herein illustrated and described.

* * * * *